United States Patent [19]
Hagenson et al.

[11] Patent Number: 5,665,600
[45] Date of Patent: Sep. 9, 1997

[54] *PICHIA PASTORIS* LINEAR PLASMIDS AND DNA FRAGMENTS THEREOF

[75] Inventors: Mary Jane Hagenson; Kathryn A. Barr, both of Bartlesville, Okla.; David W. Stroman, Richardson, Tex.; Frank H. Gaertner; Michael M. Harpold, both of San Diego, Calif.; Ronald D. Klein, Schoolcraft, Mich.

[73] Assignee: Research Corporation Technologies, Inc., Tucson, Ariz.

[21] Appl. No.: 761,528

[22] Filed: Sep. 18, 1991

[51] Int. Cl.$^6$ .................... C12N 15/63; C12N 15/81
[52] U.S. Cl. .................... 435/320.1; 435/938; 935/22; 935/66; 935/69
[58] Field of Search .................... 435/320.1, 938; 935/22, 66, 69

[56] References Cited

U.S. PATENT DOCUMENTS

| | | | |
|---|---|---|---|
| 4,418,150 | 11/1983 | Gunge | 435/256 |
| 4,477,571 | 10/1984 | Chang et al. | 435/253 |

FOREIGN PATENT DOCUMENTS

| | | | |
|---|---|---|---|
| 0103201 | 3/1984 | European Pat. Off. | |
| WO83/64261 | 8/1983 | WIPO | C12N 15/00 |

OTHER PUBLICATIONS

Worsham et al., "Killer toxin production in *Pichia acaciae* is associated with linear DNA plasmids," Current Genetics (18): 77–80 (1990).

Haymar et al., "Linear DNA plasmids of *Pichia inositovora* are associated with a novel Killer toxin activity," Current Genetics, 19:389–396 (May 1991).

Ligon et al., "Physical and Biological Characterization of Linear DNA Plasmids of the yeast, *Pichia inositovora*," Plasmid, 21(3)185–194. (1989).

Lewin, B. (1985) "Genes", second edition (John Wiley & Sons, New York), pp. 68–73, 281–283, 523–525.

EP–A–O 180 899 (Phillips Petroleum Company), published May 14, 1986.

EP–A–O 183 070 (Phillips Petroleum Company), published Jun. 4, 1986.

EP–A–O 226 752 (Phillips Petroleum Company), published Jul. 1, 1987.

Cregg et al., (1985) "*Pichia pastoris* as a host system for transformations," Molecular and Cellular Biology vol. 5, No. 12, pp. 3376–3385.

Gunge et al., "Isolation and Characterization of Linear Deoxyribonucleic Acid Plasmids from Kluyveromyces Lactis & the Plasmid Associated Killer Character", vol. 145 Journal of Bacteriology, pp. 382–390 (Jan. 1981).

Hirochika H. et al. "Analysis of Linear Plasmids Isolated Streptomyces: Association of Protein with the Ends of the Plasmid DNA", vol. 1, Plasmid 7, pp. 59–65 (1982).

Gunge, N. "DNA Plasmids", vol. 37 Ann. Reviews of Microb., pp. 253–276 (1983).

*Primary Examiner*—Mindy Fleisher
*Assistant Examiner*—Nancy J. Degen
*Attorney, Agent, or Firm*—Scully, Scott, Murphy & Presser

[57] ABSTRACT

Two novel linear DNA plasmids are described. Also, novel fragments of the plasmids containing the autonomous replication sequence (ARS), and thus capable of self-maintenance as extra chromosomal elements are provided. These novel DNA sequences of the present invention are useful in a vector for self-maintenance in *Pichia pastoris* and are also useful as plasmid vectors which can be shuttled between yeast and bacteria.

3 Claims, 5 Drawing Sheets pPP1 RESTRICTION ENDONUCLEASE MAP pPP1

FIG. 1 pPP2 RESTRICTION ENDONUCLEASE MAP

PICHIA PASTORIS LINEAR PLASMIDS AND DNA FRAGMENTS THEREOF

BACKGROUND

A basic element employed in recombinant DNA technology is the plasmid, which is extrachromosomal, double-stranded DNA found in some microorganisms. Where plasmids have been found to naturally occur in microorganisms, they are often found to occur in multiple copies per cell. Most reported naturally occurring plasmids are of covalently closed circular DNA; however, linear plasmids have been found to exist in organisms such as *Kluyveromyces lactis* and *Pichia Acaciae*.

The utility of isolated linear plasmids has traditionally revolved around their use as hybrid or shuttle vectors. These plasmids can be specifically cleaved by restriction endonucleases or other restriction enzymes, each of which recognizes a specific, unique site on the plasmid DNA. Thereafter, homologous genes as well as heterologous genes, i.e., genes derived from organisms other than the host, or gene fragments, may be inserted into the plasmid by endwise joining of the cleaved plasmid and the desired genetic material at the cleavage site or at reconstructed ends adjacent to the cleavage site. The resulting recombined DNA material can be referred to as a hybrid or shuttle vector which is then able to be expressed in a host microorganism.

In addition, linear plasmids are sources of autonomous replication sequences (ARS) which are required to produce the plasmid in daughter cells. Thus, linear plasmids are convenient vehicles for the modification of host cells. However, linear plasmids found in other microorganisms have demonstrated utility which extends beyond that of use as sources of ARS and subsequent shuttle vectors. For example, a linear DNA can serve as a linear DNA vector and was found to be stably maintained in cytoplasm. These newly developed vectors are extremely stable and have high copy numbers.

Also linear plasmids of have been found to code for a secreted killer toxin which is capable of killing a wide variety of sensitive yeast strains while immunizing the producing organism from the toxin. These linear plasmids are believed to be the source of a secretion signal which is useful in the secreted production of heterologous proteins. A killer system in which toxin production and immunity are both associated with linear double-stranded DNA was found to exist in *Pichia acacial*. The toxins produced might prove useful in the biotyping of pathogenic fungi as has been demonstrated for other *Pichia* toxins.

The uses of linear plasmids are continuously being explored. In addition to having already demonstrated their utility as shuttle vectors and sources of ARS, they are potentially useful as recombinant linear plasmids which are highly stable and maintain heterologous DNA at a high copy number; sources of secretion signals; sources of promoters for the expression of proteins; as well as utilities yet to be discovered with continued experimentation. An ongoing interest in linear plasmids and their use in recombinant DNA technology exists; therefore, providing additional linear plasmids is a significant contribution to the art.

SUMMARY OF THE INVENTION

It is therefore an object of this invention to provide two novel linear DNA plasmids of *Pichia pastoris*.

Another object of the present invention is to provide novel isolated DNA fragments of the linear plasmids which comprise the autonomous replicating sequence (ARS).

These and other objects of the present invention will become apparent from inspection of the disclosure and claims herein provided.

DETAILED DESCRIPTION

*Pichia pastoris* NRRL-11430 was deposited on Jan. 31, 1981 at the Agricultural Research Culture Collection (NRRL), 1815 N. University Street, Peoria, Ill., 61604. *Escherichia coli* LE392-pYJ8 (NRRL B-15889) was deposited on Sep. 20, 1984 at the Agricultural Research Culture Collection (NRRL), 1815 N. University Street, Peoria, Ill., 61604. *Pichia pastoris* GS115 (NRRL Y 15851) was deposited on Aug. 31, 1984 at the NRRL, 1815 N. University Street, Peoria, Ill. 61604.

In accordance with the present invention, two linear plasmids, pPP1 and pPP2 have been discovered and isolated from *Pichia pastoris*.

The discovery of pPP1 and pPP2 occurred when the total DNA of a *Pichia pastoris* cell, NRRL-11430, was isolated and examined using DNA agarose gel electrophoresis which is known to those skilled in the art and detailed in *Isolation and Characterization of Linear Deoxyribonucleic Acid Plasmids from Kluyveromyces lactis* and the *Plasmid-Associated Killer Character*, Vol. 145, No. 1, "Journal of Biotechnology", pp 382–390 (January 1981).

Once discovered, these linear plasmids were then isolated. As presently practiced, isolation of pPP1 and pPP2 is accomplished by:

subjecting *Pichia pastoris* NRRL-11430 cells to incubation utilizing methods and equipment known to those of ordinary skill in the art in conjunction with enzymatic degradation agents which include but are not limited to zymolase and glusulase; cell walls are thus made permeable allowing the linear plasmids to profuse from the cell;

treating the supernatant of the incubation mixture with proteolytic enzymes such as RNAase, and proteinase K to purify the DNA, and sodium dodecyl sulfate to solubilize the protein mixture;

centrifuging the mixture and collecting and dialyzing the supernatant against TE buffer;

precipitating the DNA from the supernatant using alcohol precipitation techniques, centrifuging the mixture and resuspending the precipitate in TE buffer and dialyzing against sucrose gradient buffer;

subjecting the DNA samples thus dialyzed to sucrose gradient centrifugation;

fractionating the sucrose gradients and analyzing the fractions on agarose gels; those fractions containing DNA are pooled and dialyzed in TE buffer, precipitated with isopropanol and centrifuged, and the pellet vacuum dried.

The DNA concentration is determined using ultraviolet spectrophotometry. The resultant isolated DNA is a mixture of linear plasmids pPP1 and pPP2. Further details and conditions for each step are recounted in Example I.

Once isolated, the DNA plasmids are cleaved into fragments via partial digestion of pPP1 and pPP2 by restriction endonucleases. Tables I through VI list those restriction endonucleases which work best as well as those which do not work at all; however, these tables merely provide the preferred endonucleases and are not intended to limit this invention in any way. The fragments are then able to be cloned for the autonomously replicating segments, (ARS), by:

precipitating the partially digested DNA using isopropanol, centrifuging the precipitate, and resuspending the pellet in TE buffer;

size fractionating the DNA fragments using sucrose gradients, and analyzing the fractions therefrom on agarose gels;

pooling like fractions containing 2–4 Kb fragments and dialyzing in TE buffer, precipitating the dialysate with isopropanol and centrifuging;

subjecting this DNA mixture to restriction endonuclease in order to digest chromosomal DNA to fragments to less than 500 base pairs in length;

transforming these 2 to 4 b linear plasmid fragments into *E. coli* and then back into *Pichia pastoris* so that those containing the ARS can be identified.

Further details and conditions for each step are recounted in Example II.

TABLE I

RESTRICTION ENDONUCLEASES WHICH DO NOT CUT pPP1

| Ava I | Hha I | Nru I | Sst I |
|---|---|---|---|
| Bam HI | Hind III | Pvu I | Sst II |
| BstE II | Kpn I | Sal I | Xba I |
| EcoRI | Nde I | Sma I | Xho I |
| FnuD II | | | |

TABLE II

RESTRICTION ENDONUCLEASES WHICH CUT pPP1 ONCE (SINGLE-CUTTERS) AND APPROXIMATE SIZE IN KILOBASES OF FRAGMENTS PRODUCED

| Apa I (1.5, 13.2) | Eco RV (1.0, 13.7) |
|---|---|
| Bal I (4.6, 10.1) | Pst I (5.7, 9.0) |
| Ban II (1.5, 13.2) | Sph I (9.6, 5.1) |

Single cutters are mapped to approximate sites on pPP1. See Figure 1. pPP1 ≅ 14.7 KB

TABLE III

RESTRICTION ENDONUCLEASES WHICH CUT pPP1 TWO OR MORE TIMES TO YIELD AT LEAST 3 FRAGMENTS

| Alu I | Hae III | Mbo I | Taq I |
|---|---|---|---|
| Ava II | Hinc II | Nco I | Hpa I |
| Bcl I | Hind II | Sau 3 A | Pvu II |
| Bgl II | Hpa II | | |

TABLE IV

RESTRICTION ENDONUCLEASES WHICH DO NOT CUT pPP2

| Apa I | Hind III | Sal I |
|---|---|---|
| Ava I | Hha I | Sma II |
| Bam HI | Nde I | Sph I |
| Cla I | Nru I | Sst I |
| Eco RI | Pst I | Sst II |
| Eco RV | Pvu I | Xba I |
| FnuD II | Pvu II | Xho I |

TABLE V

RESTRICTION ENDONUCLEASES WHICH CUT pPP2 ONCE - AND APPROXIMATE SIZE OF FRAGMENTS PRODUCED

| Bst E II | 5.3 and 4.3 Kb |
|---|---|
| Kpn I | 3.1 and 6.5 Kb |

TABLE VI

RESTRICTION ENDONUCLEASES WHICH CUT pPP2 TWO OR MORE TIMES, TO YIELD AT LEAST 3 FRAGMENTS

| Ava II | Hinc II |
|---|---|
| Bal I | Nco I |
| Bcl I | Sau 3 A |
| Bgl II | Taq I |

EXAMPLES

The following examples are provided to illustrate the practice of the invention and are not intended to limit the scope of the invention or the appended claims in any way.

The buffer and media employed in the following examples have the composition given below.

| Sucrose Gradient Buffer | 0.1 M NaCl |
|---|---|
| | 10 mM Tris (pH8) |
| | 10 mM EDTA |
| | 0.1% SDS |
| 1M Tris buffer | 121.1 g Tris base in 800 mL of |
| | $H_2O$ adjust pH to the desired value by adding concentrated (35%) aqueous HCl; allow solution to cool to room temperature before final pH adjustment; dilute to a final volume of 1L. |
| TE Buffer | 10.0 mM Tris buffer |
| | 1.0 mM EDTA |
| | (pH 7.4) |
| LB (Luria-Bertani) | 10 g Bacto-tryptone |
| | 5 g Bacto-yeast extract |
| | 8 g NaCl in 1 L of water, adjusted to pH 7.5 with NaOH |
| YPD Medium | 1% Bacto-yeast extract |
| | 2% Bacto-peptone |
| | 2% Dextrose |
| $IM_1$ (minimal medium) | IM, Salts at a final concentration of 36.7 mM $KH_2PO_4$, 22.7 mM $(NH_4)_2SO_4$, 2.0 mM $MgSO_4 \cdot 7H_2O$ 6.7 mM KCl, 0.7 mM $CaCl_2 \cdot 2H_2O$, prepared as a 10x stock solution and autoclaved; Trace Salts at a final concentration of 0.2 μM $CuSO_4 \cdot 5H_2O$, 1.25 μM KI, 4.5 μM $MnSO_4 \cdot \sqrt{}\ H_2O$, 2.0 μM $NaMoO_4 \cdot _{2H2}O$, 0.75 μM $H_3BO_3$, 17.5 μM $ZnSO_4 \cdot 7H_2O$, 44.5 μM $FeCl_3 \cdot 6H_2O$, prepared as a 400x stock solution and filter sterilized; 0.4 μg/mL biotin; and 2% dextrose. |

The following abbreviations are used throughout the examples with the following meaning:

EDTA: ethylenediamine tetraacetic acid
SDS: sodium dodecyl sulfate
DTT: dithiothreitol
AB3: bacto-beef extract, 1.5 g.; bacto-yeast extract, 1.5 g.; bacto-peptone,
5 g.; bacto-dextrose, 1 g.; sodium chloride 3.5 g.; dipotassium phosphate, 3.68 g.; monopotassium phosphate, 1.32 g.

*Pichia pastoris* was grown in YPD (rich) or IM₁ (minimal) media.

*E. coli* was cultured in either LB medium or 2B medium (0.2% NH₄PO₄, 1.2% Na₂HPO₄, 0.013% MgSO₄·H₂O, 0.074% CaCl₂·2H₂O, 1 µg/mL thiamine and 0.4% dextrose).

Example I

Isolation of Linear Plasmids pPP1 and pPP2

*Pichia pastoris* NRRL Y-11430 cells were divided into approximately 30 gram lots and placed in 500 ml bottles. These cells were washed one time with 500 ml of 0.1M Tris(pH 8) and 1% β-mercaptoethanol. The cells were then centrifuged for about 5 minutes. The pellet (30 g) was washed and then resuspended in about 180 ml of 0.6M potassium chloride. The cells of the resuspension were subsequently centrifuged for 5 minutes at about 4000 g, and then resuspended in 250 ml of 0.6M KCl and Zymolyase (Zymolase 60,000 manufactured by Miles Laboratories) was added to a concentration of about 500 µg per ml. The cells were then incubated with Zymolase (Miles Laboratories) for 40 minutes in a 37° C. water bath. After incubation, the incubation mixture was centrifuged at about 10,000 g and the supernatant treated with RNAase A added at a concentration of about 100 pg per ml at 37° C. for 1 hour. The supernatant was then treated with a Proteinase K solution having a concentration of about 50 pg per ml at room temperature for 15 minutes. Sodium dodecyl sulfate was then added to achieve a concentration of 0.1% and the mixture was centrifuged for about 20 minutes at about 10,000 g. The supernatant was dialyzed against about 8 liters of TE buffer overnight. During this dialysis process the TE buffer was changed two times with 8 liter changes. The DNA was precipitated from the supernatant by adding an equal volume of isopropanol and one tenth volume of 5M NaCl, and centrifuging the mixture for about 1 hour in order to precipitate the DNA. The pellets resulting from the precipitation were resuspended in 70 ml of the TE buffer and dialyzed overnight against 8 liters of sucrose gradient buffer. The dialyzed DNA samples were added to centrifuge tubes for sucrose gradient centrifugation in the following order such that distinct layers were maintained: 5 ml of 40% sucrose cushion, 20 ml of 15%–30% linear gradient, and 5 ml sample of dialyzed DNA to a final concentration of 10% sucrose. The samples were then centrifuged at 130,000 g for about 18 hours. The gradients were fractionated and the fractions analyzed on 0.8% agarose gels. Approximately 400 DNA-containing fractions with a total volume of 90 ml were pooled and dialyzed against four 8 liter changes of TE buffer for a total time of about 56 hours. The dialyzed DNA was then precipitated with an equal volume of isopropanol and a one tenth volume of 5M NaCl, and the solution was centrifuged at about 17,000 g for about 45 minutes. The precipitated pellet containing DNA was vacuum dried, washed with a small volume of TE buffer and then resuspended in 7 ml TE buffer. The DNA concentration was then determined using ultraviolet spectrophotometry, by the method of Manjarls T., et al., "Molecular Cloning, A. Laboratory Manual", Cold Spring Harbor Laboratory, Cold Spring Harbor, N.Y., (1982). This DNA was a mixture of the linear plasmids pPP1 and pPP2.

Figure 1:
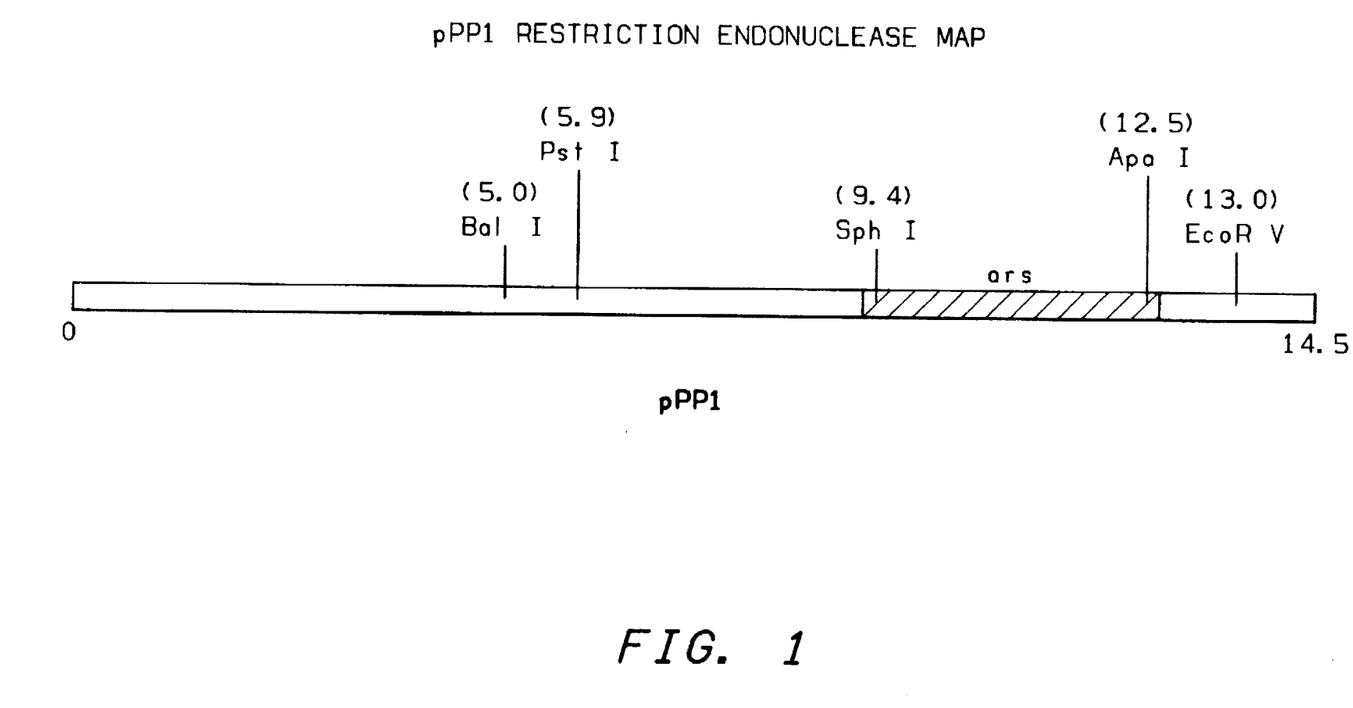
FIG. 1: Restriction Endonuclease Map of pPP1.
Figure 2:
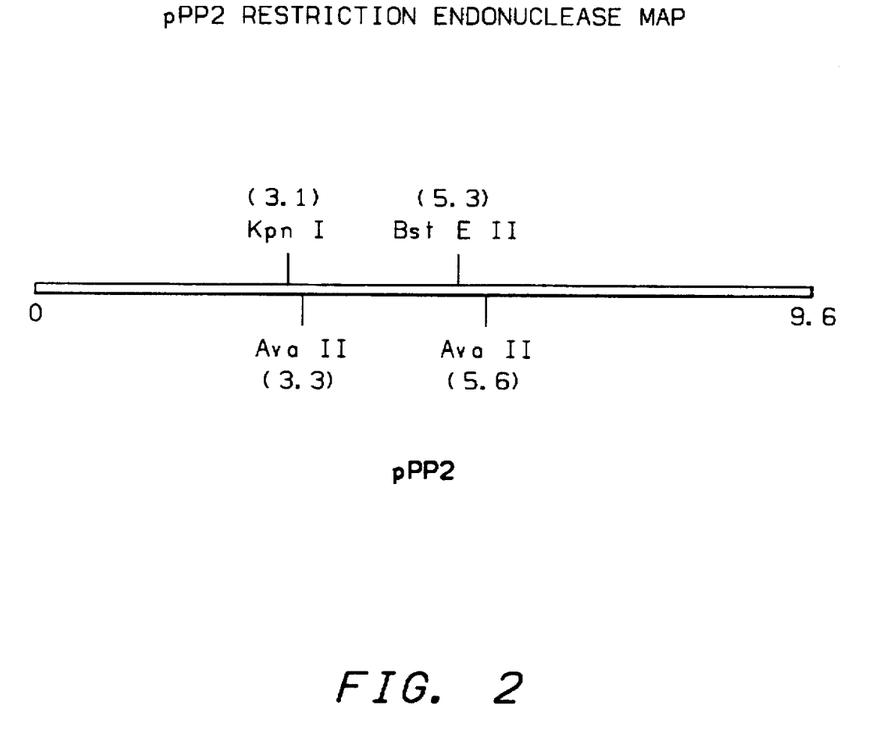
FIG. 2: Restriction Endonuclease Map of pPP2.
Figure 3:
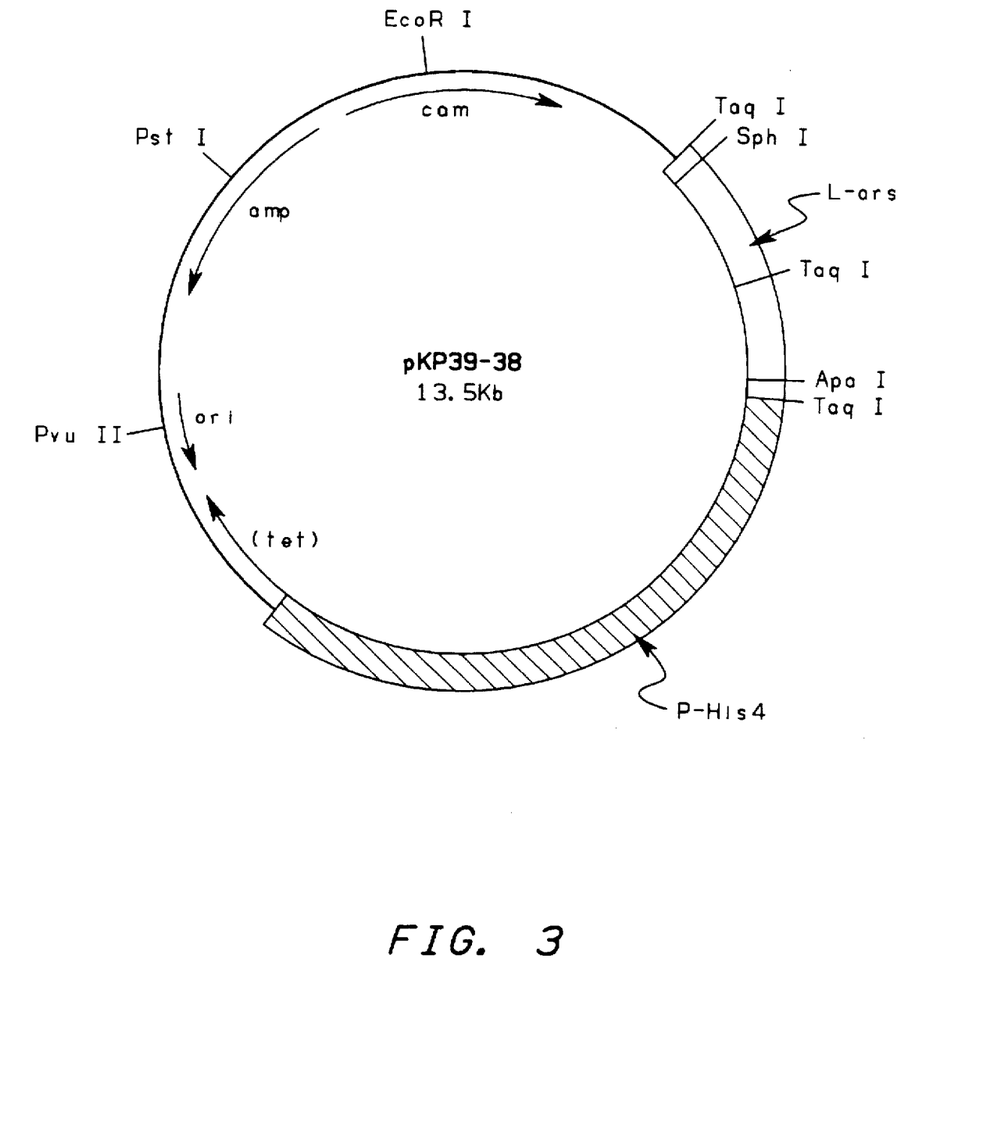
FIG. 3: Map of circular plasmid pKP39-38.
Figure 4:
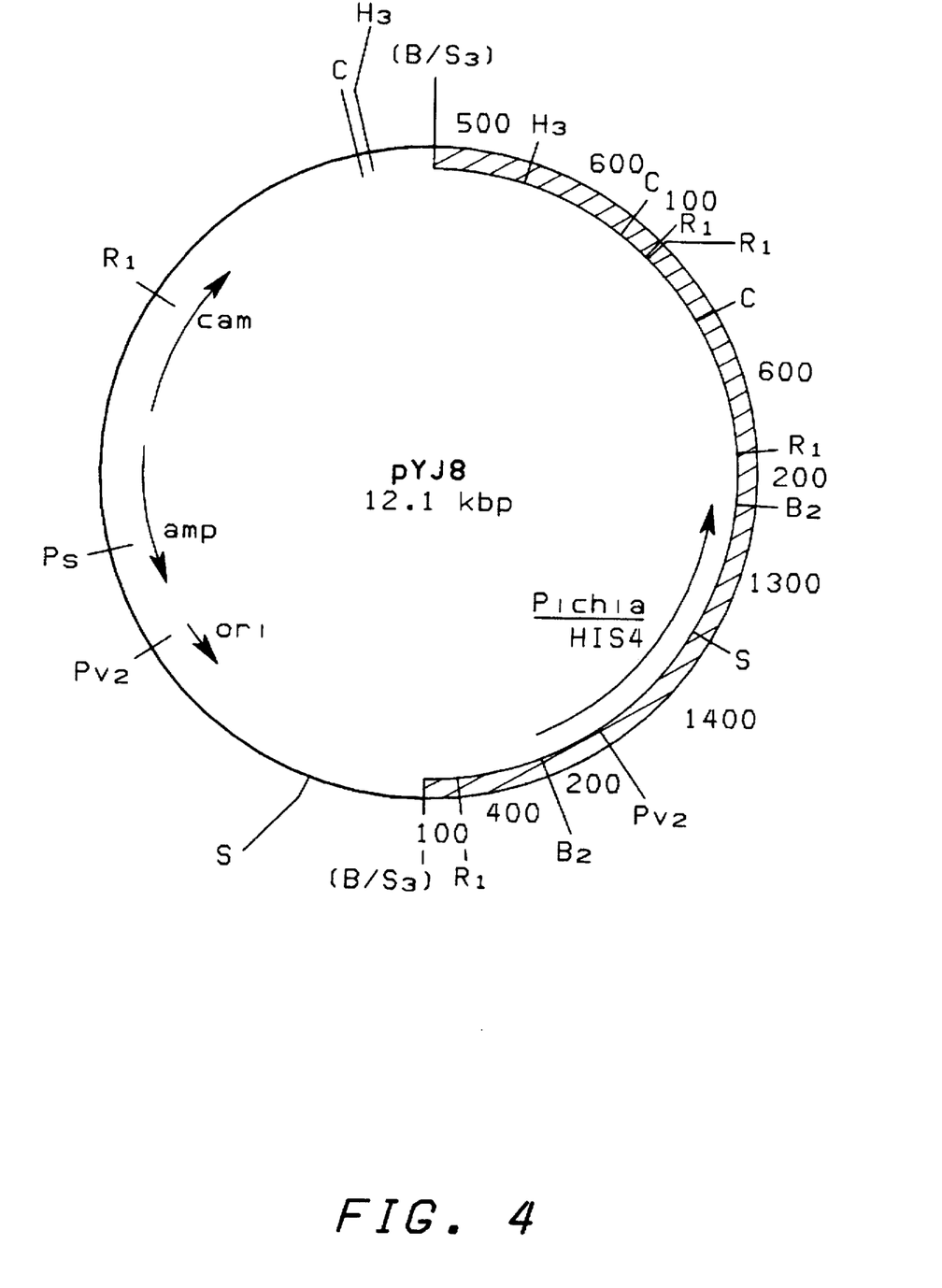
FIG. 4: Map of circular plasmid pYJ8.
Figure 5:
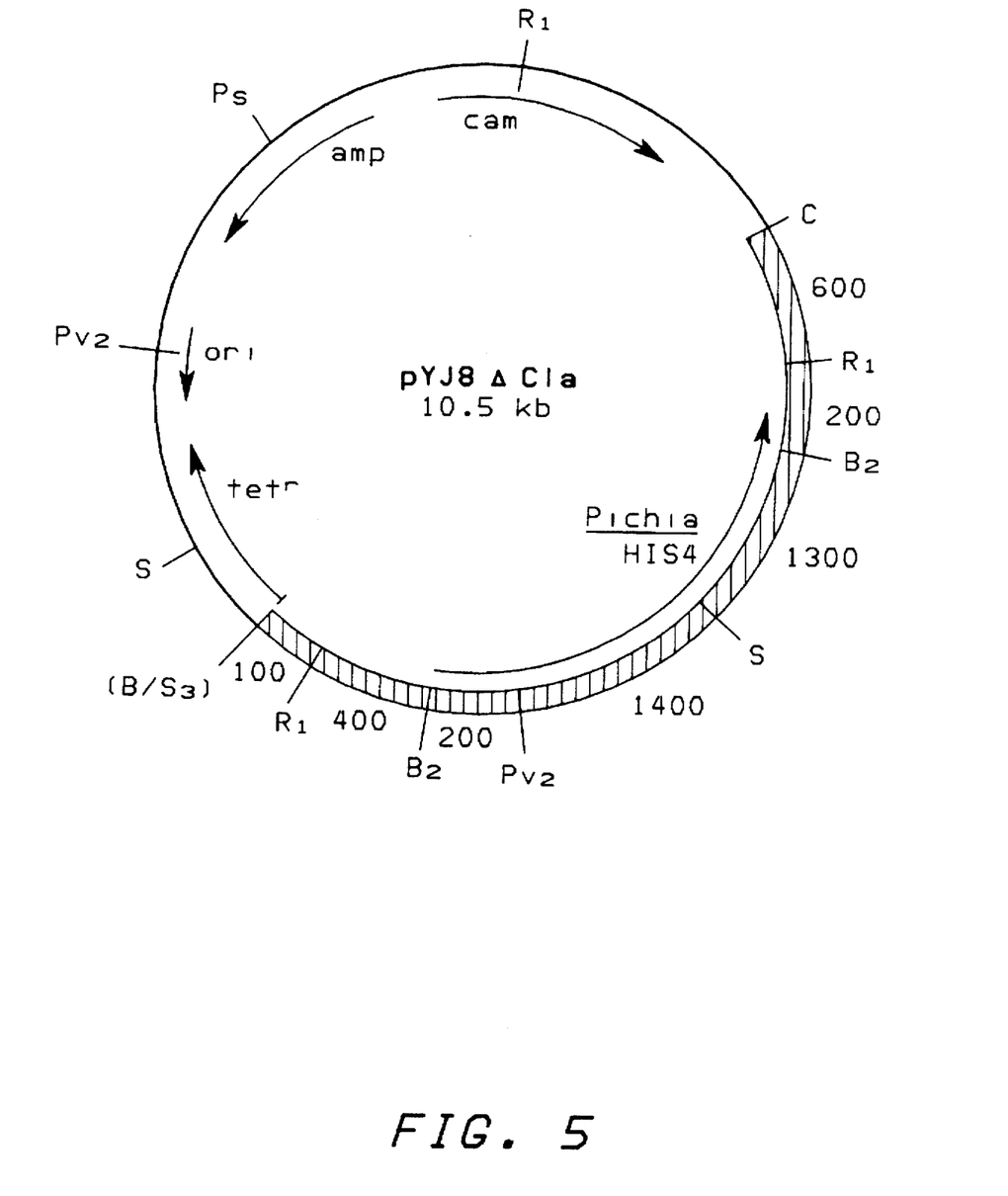
FIG. 5: Map of circular plasmid pYJ8ΔCla.

Restriction maps of pPP1 and pPP2 are represented in FIGS. 1 and 2, respectively. The frequency of the occurrence of DNA cleavage sites with various restriction endonucleases are given in Tables I–III for pPP1 and Tables IV–VI for pPP2.

Example II

Isolation of the ARS of pPP1 and pPP2 Fragments

Partial TaqI digestion of pPP1 and pPP2 was performed in a final volume of 1,000 µl comprising 100 µl of DNA (from the pPP1 and pPP2 mixtures), with 100 µl of a 10× low salt buffer, 50 µl of a 2 mg/ml Bovine Serum Albumin (BSA) solution and approximately 750 µl H₂O. Approximately 30 units of TaqI enzyme were added to the reaction mixture. The reaction was kept at 65° C. for about 25 minutes to effectuate partial digestion and then placed on ice in order to curb any further enzymatic degradation. The DNA was precipitated with an equal volume of isopropanol, and a one tenth volume of 5M NaCl and the mixture was centrifuged for about 1 hour at about 17,000 g. The pellet was resuspended in about 2 ml of TE buffer. Linear sucrose gradients (10%–30%) were prepared for size fractionation of DNA fragments. Gradients were centrifuged for 18 hours at 130,000 g. From these gradients 10 drop fractions were collected and every third fraction was analyzed on 0.8% agarose gels. Like fractions containing the 2–4 kb fragments were pooled and dialyzed for about 7 hours against the TE buffer with four 4 liter changes of buffer. At the end of this dialysis fractions were precipitated with an equal volume of isopropanol containing 0.3M ammonium acetate. This solution was centrifuged for approximately 1 hour to precipitate the DNA. The pellet was vacuum dried and resuspended in 0.5 ml of TE buffer.

500 µl of the pooled 2–4 kB DNA was digested with 10 µl of HhaI in the presence of 60 µl of 10× medium salts buffer and 30 µl BSA (2 mg/ml). The sample was incubated at 37° C. for 2 hours in order to digest chromosomal DNA to fragments less than 500 bp in length. (It should be noted that pPP1 and pPP2 DNAs were not cut by the HhaI). DNA was ethanol precipitated (as above) and the pellet vacuum dried and resuspended in TE buffer.

The ligation of the 2–4 kb Taq1 fragments with calf intestinal alkaline phosphatase, (CIP), treated vector was as follows: 5 µl of vector DNA pYJ8ΔCla (pYJ8ΔCla was prepared by digesting pYJ8 (NRRL B-15889) with ClaI, isolating the vector backbone, and ligating the end of the vector, i.e. a pYJ8 vector cleaved with Cla to render only one cleavage site, obtained by ClaI digestion, using standard digestion procedures well known to those skilled in the art, of pYJ8 a shuttle vector containing His4 *Pichia* gene and resistance genes of chlorampheninol and amphicillin both of which are active in *E. coli*, and religatins with subsequent omission of a#1.6 KB ClaI unique fragment cut with ClaI and treated with CIP to prevent self ligation) was combined with 4.5 µl of ligase salts 10×, 2.5 µl of BSA (2 pg/µl), 1 µl of ATP (50 mM), and water to 45 µl total volume. The ligation mixtures, containing either 1, 2, or 10 µl of the 2–4 kb Taq1 fragments were heated to 42° C. for 5 minutes, and cooled to room temperature. 5 µl spermidine (40 mM) and 200 units T4 DNA ligase were added and the ligations were performed for 16 hours at 12.5° C. in a circulating glycol bath.

*E. coli* 848 was then transformed with each of the above three ligation mixtures containing the 2–4 kb fragments, the CaCl method known to those of skill in the art, and described in Maniatis. Transformants were selected on plates containing 40 pg/ml of LB-ampicillin (LB-AMP). Selected transformants were transferred to master LB-AMP plates. Pooled colonies from these master plates were used to inoculate 700 ml of AB3-AMP (40 pg/ml) (1 liter flask). From this, the pooled plasmids now referred to as pKP39 plasmids were isolated using the alkaline SDS isolation as described on page 368 of Maniatis and the plasmid pool of pKP39 DNA was purified on CsCl gradients.

*Pichia pastoris* strain GS115 (his4) (NRRL-aY-15851) was transformed as described in Gregg, U.S. Pat. No. 4,929,555 issued on May 29, 1990 and assigned to Phillips Petroleum Company, with these pKP39 pooled plasmids in order to select plasmids containing the *Pichia* linear ARS element. Transformants were selected on histidine deficient plates. Forty individual transformants, designated GS115 (pKP39-1) through GS115 (pKP39-40), were isolated and subsequently grown at 30° C. for about 40 hours in 10 ml IM1+1% glucose +1 ml 2× His assay medium. Total yeast DNA was isolated from 1 ml of each pKP39-N culture. Each pKP39-N DNA was subsequently transformed into *E. coli* for large scale isolation.

Reasonable variations and modifications, not departing from the essence and spirit of the invention, are contemplated to be within the scope of patent protection sought.

That which is claimed is:

1. An isolated linear DNA plasmid obtainable from *Pichia pastoris* NRRL Y-11430 and having an approximate length of 14,000 base pairs and the restriction map of FIG. 1.

2. An isolated linear DNA plasmid obtainable from *Pichia pastoris* NRRL Y-11430 and having an approximate length of 10,000 base pairs and the restriction map of FIG. 2.

3. Isolated ARS DNA fragment derived from the linear DNA of claim 1.

* * * * *

UNITED STATES PATENT AND TRADEMARK OFFICE
CERTIFICATE OF CORRECTION

PATENT NO. : 5,665,600

DATED : September 9, 1997

INVENTOR(S) : May J. Hagenson, et al.

It is certified that error appears in the above-identified patent and that said Letters Patent is hereby corrected as shown below:

Column 2, lines 23-25: delete "In accordance with the present invention, two linear plasmids, pPP1 and pPP2 have been discovered and isolated from Pichia pastoris." and line 14 insert the following: --In accordance with the present invention, two linear plasmids, pPP1 and pPP2 have been discovered and isolated from Pichia pastoris.--

Column 4, line 45: "IM," should read --$IM_1$--

Column 4, line 51: "$\sqrt{}$H" should read --•H--

Column 4, line 52 "$2H2$" should read --$2H_2$--

Column 5, line 4: "•H" should read --•7H--

Column 5, lines 25 & 29: "pg" should read --µg--

UNITED STATES PATENT AND TRADEMARK OFFICE
CERTIFICATE OF CORRECTION

PATENT NO. : 5,665,600
DATED : September 9, 1997
INVENTOR(S) : May J. Hagenson, et al.

It is certified that error appears in the above-identified patent and that said Letters Patent is hereby corrected as shown below:

Column 5, lines 58-59: "Manjarls" should read --Maniatis--

Column 6, lines 62 & 65 "pg" should read --µg--

Signed and Sealed this

Twenty-eighth Day of March, 2000

Attest:

Q. TODD DICKINSON

Attesting Officer

Commissioner of Patents and Trademarks